(12) United States Patent
Shmidman

(10) Patent No.: US 8,187,212 B2
(45) Date of Patent: May 29, 2012

(54) PAIN-ALLEVIATING ORTHOPAEDIC APPLIANCE

(75) Inventor: Akiva Shmidman, Baltimore, MD (US)

(73) Assignee: Beactive Technologies LLC, Baltimore, MD (US)

(*) Notice: Subject to any disclaimer, the term of this patent is extended or adjusted under 35 U.S.C. 154(b) by 361 days.

(21) Appl. No.: 12/365,132

(22) Filed: Feb. 3, 2009

(65) Prior Publication Data

US 2009/0287124 A1 Nov. 19, 2009

Related U.S. Application Data

(60) Provisional application No. 61/052,688, filed on May 13, 2008.

(51) Int. Cl.
*A61F 5/00* (2006.01)
*A61F 13/06* (2006.01)
*A61F 5/37* (2006.01)

(52) U.S. Cl. ........... 602/23; 602/26; 602/61; 602/62; 602/63; 128/882

(58) Field of Classification Search ............ 602/23, 602/26, 60, 62, 63, 5, 20, 61; 606/201, 203, 606/204; 128/106.1, 95.1, 112.1
See application file for complete search history.

(56) References Cited

U.S. PATENT DOCUMENTS

| | | | | |
|---|---|---|---|---|
| 3,970,081 A * | 7/1976 | Applegate, Jr. | ............ | 128/95.1 |
| 4,275,716 A * | 6/1981 | Scott, Jr. | ............ | 602/26 |
| 4,370,978 A * | 2/1983 | Palumbo | ............ | 602/26 |
| 4,777,946 A * | 10/1988 | Watanabe et al. | ............ | 602/62 |
| 5,085,210 A * | 2/1992 | Smith, III | ............ | 602/26 |
| 5,667,484 A | 9/1997 | Brossard | | |
| 5,865,775 A * | 2/1999 | Peoples et al. | ............ | 602/20 |
| 6,077,242 A | 6/2000 | Falk et al. | | |
| 6,755,800 B2 * | 6/2004 | Weaver et al. | ............ | 602/62 |
| 7,862,529 B2 * | 1/2011 | Brown | ............ | 602/26 |
| 2002/0077575 A1 * | 6/2002 | Cox | ............ | 602/26 |
| 2005/0070831 A1 | 3/2005 | Cormier et al. | | |
| 2011/0125071 A1 * | 5/2011 | Chisena et al. | ............ | 602/2 |

OTHER PUBLICATIONS

International Preliminary Report on Patentability together with the Written Opinion of the International Searching Authority (ISA) for PCT/US2009/043638 mailed on Nov. 17, 2010 (6 pages).
International Search Report from related PCT Application No. PCT/US2009/43638 dated Dec. 16, 2009.

* cited by examiner

*Primary Examiner* — Patricia Bianco
*Assistant Examiner* — Kari Petrik
(74) *Attorney, Agent, or Firm* — Edwards Wildman Palmer LLP; Scott D. Wofsy; Jason LaBerteaux

(57) ABSTRACT

An orthopaedic appliance includes a body, a protrusion extending inwardly from the body, positioned on the body to apply pressure on a proximal portion of the soleus muscle, and means for applying pressure to the protrusion.

18 Claims, 2 Drawing Sheets

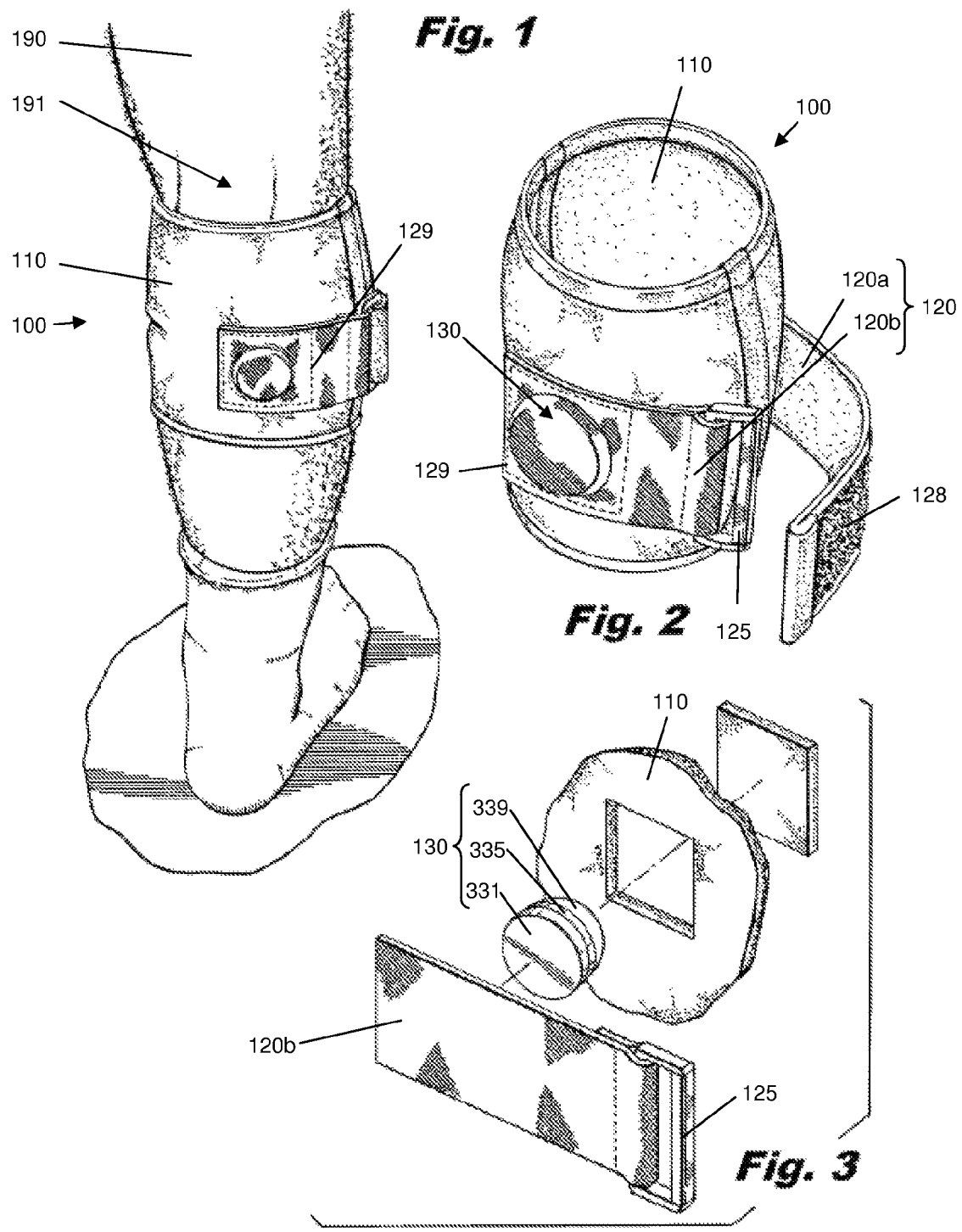

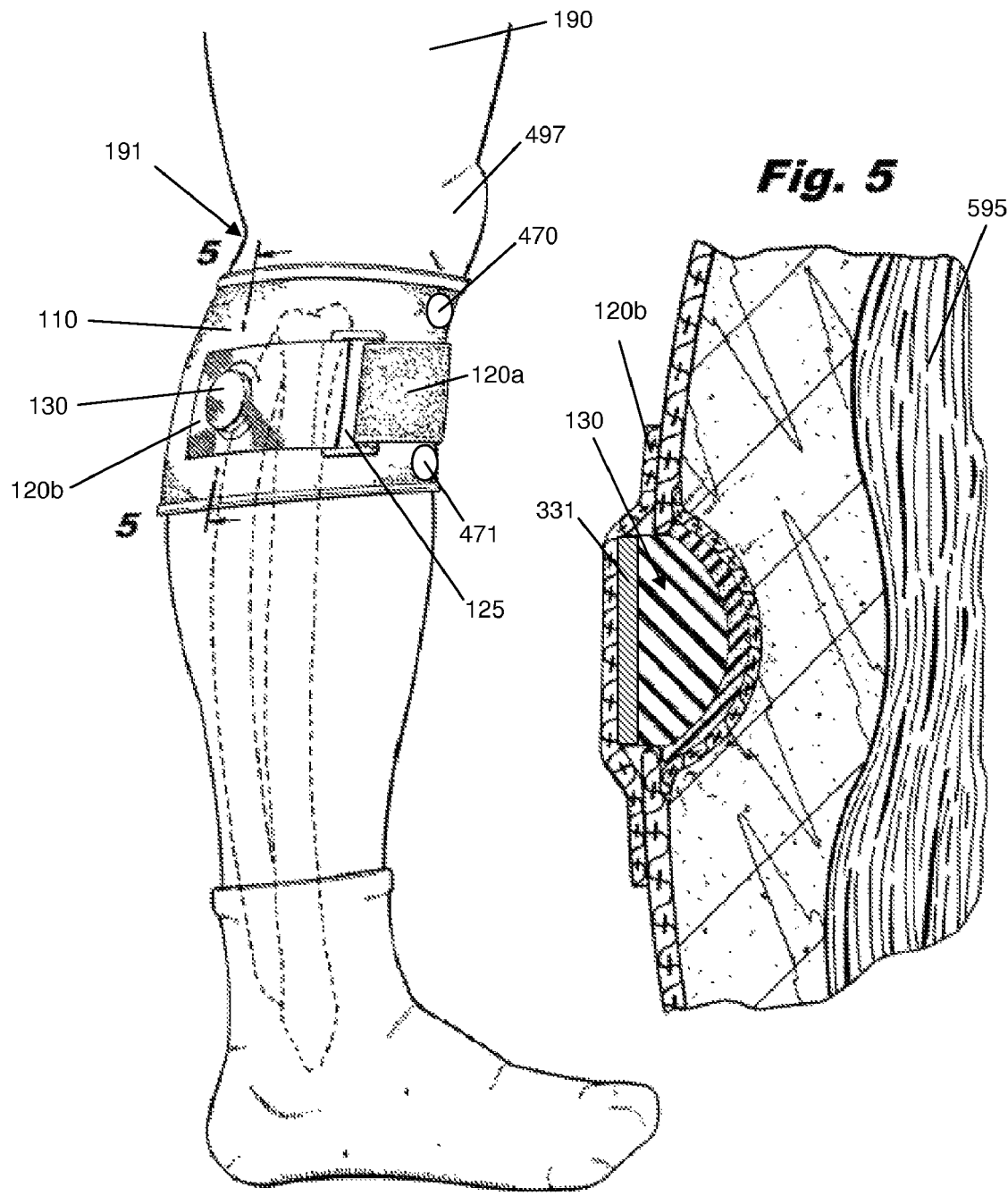

PAIN-ALLEVIATING ORTHOPAEDIC APPLIANCE

CROSS-REFERENCE TO RELATED APPLICATIONS

This application claims the benefit of priority to U.S. Patent Application Ser. No. 61/052,688, filed May 13, 2008, which is incorporated herein by reference in its entirety.

FIELD OF THE INVENTION

The present invention relates to orthopaedic appliances such as braces. Particularly, the present invention is directed to an orthopaedic appliance that reduces pain by reducing tension on an affected nerve.

DESCRIPTION OF RELATED ART

A variety of orthopaedic appliances, such as braces (orthoses), are known in the art for providing support, protection, and/or stability to various joints of the body. Braces of varying sizes and shape are available for joints including the wrists, knees, ankles, and others. Many braces serve to stabilize a joint, to allow it to heal, while some braces are configured for load sharing across a joint to reduce the load on the joint to facilitate healing.

Applicant recognizes that a common complaint of physical therapy patients is lower back and/or buttock pain. There are many people who suffer from lumbar pain and radiating symptoms. However, lumbar braces available today are large, focus on relaxing the paraspinal muscles, and are difficult to hide under everyday clothing.

Applicant further recognizes that this experienced pain is often associated with the sciatic nerve and caused by pathology at a different location—for example at the knee. Applicant appreciates that spasming of the soleus muscle of the calf can cause a patient's fibula to be pulled toward the posterior, causing tension on the peroneal nerve (common fibular nerve) at the tibiofibular joint.

The peroneal nerve is a continuation of a portion of the sciatic nerve, which continues upward, originating from the lumbar portion of the spinal column. Accordingly, this increased neural tension often produces symptoms of lower back and/or buttock pain.

Accordingly, there remains a need in the art for a therapeutic device for treating a pathological condition caused by a spasming soleus muscle on the peroneal nerve, to thereby treat the pain experienced by a patient. The present invention provides a solution for this need.

SUMMARY OF THE INVENTION

The purpose and advantages of the present invention will be set forth in and apparent from the description that follows. Additional advantages of the invention will be realized and attained by the methods and devices particularly pointed out in the written description and claims hereof, as well as from the appended drawings.

To achieve the foregoing advantages and in accordance with the purpose of the invention as embodied, the invention includes in one aspect, an orthopaedic appliance for reducing pathological tension on a patient's peroneal nerve. The orthopaedic appliance includes a body configured for placement below the popliteal crease of a patient's leg, a protrusion or "build-up" extending inwardly from the body, positioned on the body to apply pressure on a proximal portion of the soleus muscle, and an adjustable strap portion extending at least partially around the circumference of the body.

It should be appreciated by the reader that the term "brace" can be applied to devices in accordance with the invention. It should be understood, however that devices constructed in accordance with the invention may partially stabilize the knee joint, as will be discussed in more detail below, but are most effective in reducing spasming of the soleus muscle, which thereby reduces the symptoms caused by that spasming.

The invention includes, in another aspect, an orthopaedic appliance having a body, a protrusion extending inwardly from the body, positioned on the body to apply pressure on a proximal portion of the soleus muscle, and means for applying pressure to the protrusion.

The body can be configured for placement below the popliteal crease of a patient's leg. The protrusion is positioned to apply pressure on a proximal portion of the soleus muscle near its origin at the proximal fibula. The protrusion can be positioned to apply pressure at a point between about 5.0 and 7.5 centimeters below the fibular head.

The orthopaedic appliance can further include indicia on the body to guide placement of the appliance on the leg of the patient. The indicia can be a marking on a front side of the body, placed to be in substantial alignment with a centerline of the patient's knee.

The means for applying pressure can include a first strap extending laterally from a medial side of the body and a second strap portion extending from a dorsal side of the body, extending over the protrusion and toward the first strap portion. The means for applying pressure can further include a connecting element provided to secure the first strap portion to the second strap portion. The connecting element can be a substantially rigid eyelet, or other suitable connection.

The means for applying pressure can include a repositionable fastener to allow adjustment of tension in the strap portions. The repositionable fastener can be a hook-and-loop type fastener, for example.

Alternatively, the means for applying pressure can include a band that extends at least partly around the circumference of the body. The band can be partially or fully formed from a resilient material, such as polychloroprene rubber, for example. Alternatively or additionally, at least a portion of the band can be formed of a woven material, which can, for example, be woven nylon.

The means for applying pressure can include an adjustable band that extends at least partly around the circumference of the body. The adjustable band can include two portions. Alternatively or additionally, the adjustable band can extend completely around the body.

Alternatively or additionally, the means for applying pressure can include a resilient component in the body of the orthopaedic appliance for exerting circumferential forces (hoop tension) around the body, to maintain a sufficient amount of inwardly directed pressure on the protrusion or "build-up" to impinge the proximal portion of the soleus muscle near its fibular origin at the fibular head and proximal fibula to release tension on and reduce spasming thereof. That is, it is particularly conceived that the placement of the aforementioned protrusion will be most effective when placed over the soleus muscle near the upper portion thereof. However, it is to be understood that the subject invention can be advantageously implemented to apply pressure to other locations along the soleus muscle, or alternatively to various locations on other muscles or muscle groups.

The force applied to the leg by the protrusion is preferably between about 1 and 10 pounds per square inch (between about 7.0 kPa and 70 kPa), but naturally is not necessarily limited to this range. More preferably the force applied by the protrusion is between about 3 and 7 pounds per square inch (between about 20 kPa and 50 kPa). In accordance with one preferred aspect, the force applied by the protrusion is about 5 pounds per square inch (about 35 kPa). In accordance with the invention, the area over which the force is applied is between about 1.0 and 3.0 square inches (6.45 and 20.0 square centimeters). In accordance with a preferred embodiment, the radius of the protrusion is about 0.8 inches (2.0 cm), with an area of about 2.0 square inches (about 12.0 square centimeters).

The protrusion can include a resilient portion, and provided on an inward-facing portion of the orthopaedic appliance. The protrusion is, in preferred embodiments, smoothly contoured so as to reduce potential for causing trauma to the patient. The protrusion can include a rigid portion on the outer side thereof for providing a stable backing to exert even pressure to the soleus muscle near its origin at the fibula.

The body can be formed of a compliant material to minimally impede blood circulation. The body can be formed of a neoprene rubber.

In accordance with a further aspect, the invention includes a method of treating pain associated with impingement of the peroneal nerve of a patient, including providing an orthopedic appliance having a protrusion on an inner surface thereof, orienting the orthopedic appliance so that the protrusion impinges a proximal portion of the soleus muscle of the patient slightly distal its origin at the proximal fibula, and applying pressure to the soleus muscle through the protrusion of the orthopedic appliance.

In accordance with this aspect, the protrusion can be oriented to impinge the soleus muscle between about 2.0 to 3.0 inches (about 5.0 and 7.5 cm) below the fibular head.

In accordance with the invention, the orthopaedic appliance can be dimensioned such that the protrusion is applied closer to one edge of the appliance than the other—such as by about 2.0 to 3.0 inches (about 5.0 and 7.5 cm) from one edge and about 1.0 to 2.0 inches (2.5 and 5.0 centimeters) from the opposite edge.

The body of the appliance can be dimensioned such that this position of the protrusion falls off-center with respect to the height of the appliance. That is, the size and quantity of material can be minimized by reducing the size of the appliance, particularly the portion of the body that extends downward from the protrusion.

The protrusion is oriented laterally outward, with respect to the body of the appliance. Accordingly, if the protrusion is eccentric with respect to the height of the appliance, use for both left and right legs is complicated. Accordingly, as an alternative, and in accordance with a preferred aspect of the invention, the body of the appliance can be sized such that the protrusion is situated in the center of the body, with respect to its height. In this manner, the appliance can be rotated—that is, turned "upside-down," and used for the opposite leg—that is, the other of the left or right leg.

When indicia are provided on the body of the appliance, separate indicia can be provided for use with the left leg, and with the right leg. For example, a marking indicating the "up" direction for use on each respective leg can be provided on the body of the appliance.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the method and system of the invention. Together with the description, the drawings serve to explain the principles of the invention, wherein:

FIG. 1 is a rear isometric view of a representative embodiment of a pain-alleviating orthopaedic appliance in accordance with the present invention, illustrated placed on a leg of a patient;

FIG. 2 is a view of the pain-alleviating orthopaedic appliance of FIG. 1 shown alone, with a tensioning strap thereof shown in an open position;

FIG. 3 is an exploded view of a portion of the pain-alleviating orthopaedic appliance of FIG. 1, illustrating an example construction of a protrusion element thereof for impinging a proximal portion of the soleus muscle, distal its origin at the proximal fibula;

FIG. 4 is a side view of the pain-alleviating orthopaedic appliance of FIG. 1 illustrating positioning of the protrusion element with respect to the fibula of a patient; and FIG. 5 is a cross-sectional view taken along line 5-5 of FIG. 4, illustrating, for the purpose of providing an example, the manner in which the protrusion element impinges the soleus muscle.

DETAILED DESCRIPTION OF THE PREFERRED EMBODIMENT

Reference will now be made in detail to the present preferred embodiments of the invention, an example of which is illustrated in the accompanying drawings. The method and corresponding steps of the invention will be described in conjunction with the detailed description of the system.

The devices and methods presented herein may be used for treatment of pain associated with spasming of the soleus muscle of the calf. Such pain can be experienced by the patient in a number of places, including in the buttocks or lower back.

In accordance with the invention, the invention includes, in one aspect, an orthopaedic appliance for reducing pathological tension on a patient's peroneal nerve. The orthopaedic appliance includes a body configured for placement below the popliteal crease of a patient's leg, a protrusion extending inwardly from the body, positioned on the body to apply pressure on a proximal portion of the soleus muscle, and an adjustable strap portion extending at least partially around the circumference of the body.

For the purposes of explanation and illustration, not limitation, a partial view of an orthopaedic appliance in accordance with the invention is shown in FIGS. 1-4. The orthopaedic appliance is designated generally by reference number 100, includes a body 110, a protrusion 130 extending inwardly from the body 110, positioned on the body 110 to apply pressure on a proximal portion of the soleus muscle, slightly distal its origin at the proximal fibula. The brace includes means for applying pressure to the protrusion, which in the illustrated embodiment is accomplished by way of strap portions 120a and 120b, and an eyelet 125. The body 110, further can aide in applying pressure to the protrusion 130 by way of its inherent material properties—for example, the body can be made from an elastic material such as polychloroprene (e.g. Neoprene) rubber.

In the illustrated embodiment, the body 110 is configured for placement below the popliteal crease 191 of a patient's leg 190. The protrusion 130 is positioned to apply pressure on a proximal portion of the soleus muscle (595 in FIG. 5) near its origin at the proximal fibula. The protrusion 130, in accordance with a preferred embodiment, is positioned to apply pressure on the soleus muscle at a point between about 2.4 and 4.0 inches (about 6.0 and 10.0 centimeters) from the edge of the device—that is, in use, about the same distance as the protrusion's placement below the popliteal crease 191. In accordance with one embodiment, and depending on the overall dimensions of the orthopaedic appliance, the protrusion 130 is centered at a position about 3.0 inches (about 8.0 cm) from the edge of the device. In general, in accordance with the invention, the placement of the protrusion 130 is such that it sits between about 0 and 4.0 inches (about 0 and 20.0 centimeters) below the popliteal crease.

In accordance with the invention, the body 110 of the orthopaedic appliance 100 can be dimensioned such that the protrusion is applied closer to one edge of the appliance than the other—such as by about 2.0 to 3.0 inches (about 5.0 and 7.5 cm) from one edge and about 1.0 to 2.0 inches (2.5 and 5.0 centimeters) from the other edge.

The body 110 of the appliance 100 can be dimensioned such that its position falls off-center with respect to the height of the body 110. That is, the size and quantity of material can be minimized by reducing the size of the appliance 100, particularly the portion of the body 110 that extends downward from the protrusion 130.

The protrusion 130 is oriented laterally outward, with respect to the body 110 of the appliance 100. Accordingly, if the protrusion 130 is eccentric with respect to the height of the appliance 100, use for both left and right legs is complicated. Accordingly, as an alternative, and in accordance with a preferred aspect of the invention, the body 110 of the appliance 100 can be sized such that the protrusion 130 is situated in the center of the body 110, with respect to its height. In this manner, the appliance 100 can be rotated—that is turned "upside-down," and used for the opposite leg—that is, the other of the left or right leg.

The orthopaedic appliance 100 can further include indicia 470 (FIG. 4) on the body 110 to guide placement of the appliance on the leg of the patient. The indicia 470 can be a marking on a front side of the body 110, such as a specific alignment marking or a logo that is understood by the user to be usable as a guide for alignment of the orthopaedic appliance. For example, it is particularly envisioned that when a logo or other indicia 470 is substantially aligned with a centerline of the patient's knee 497, the protrusion 130 is in at least approximate proper alignment with respect to the knee 497 so as to impinge the soleus muscle as needed to therapeutically affect a spasming muscle, and to alleviate the pain associated therewith.

When indicia 470 are provided on the body 110 of the appliance 100, separate indicia 471 can be provided for use with the left leg, and with the right leg. For example, a marking, such as one including words or a directional symbol such as an arrow—indicating the "up" direction for use on each respective leg, can be provided on the body 110 of the appliance 100, as illustrated, for example in FIG. 4.

The first and second strap portions 120a, 120b serve to provide adjustable pressure on the orthopaedic appliance, and thus on the protrusion 130, which provides an adjustability of the pressure impinging the soleus muscle. In the illustrated embodiment, the strap portions 120a, 120b join at the eyelet, but are not contiguous with one another on the opposite (medial) side thereof. The discontinuity of the strap portions 120a, 120b, joined instead on the medial side by the body 110 itself, rather than by a continuation of the strap, advantageously prevents any undesirable reduction to blood circulation in the area. As set forth above, the material of the body 110 can be an elastic material such as polychloroprene, for example.

As illustrated, the first strap portion 120a extends laterally from a medial side of the body and a second strap portion 120b extends from a dorsal side of the body 110, over the protrusion 130 and toward the first strap portion 120a. A connecting element 125 is provided to secure the first strap portion 120a to the second strap portion 120b. The connecting element 125, as illustrated is a substantially rigid eyelet, allowing the first strap portion 120a to be looped therethrough, folded back on and secured to itself to adjust the tension thereof. A repositionable fastener 128 can be provided in connection with the strap portion, such snaps, belts, hook-and-loop type fasteners or others.

The band portions 120a, 120b are preferably formed of a material that is relatively resistant to strain, such as a woven nylon material, for example. Alternatively, a resilient material, such as neoprene or other suitable material can be used, provided that sufficient pressure can be exerted on the protrusion 130, and in-turn the soleus muscle.

As set forth above, the strap can extend partially around the circumference of the body 110. Alternatively or additionally, the adjustable band can extend completely around the body 110.

As embodied, the patient loosens the strap 120, and places the orthopaedic appliance 100 over his foot, pulling the orthopaedic appliance 100 up his leg, and positioning it as described above, so that the protrusion 130 is arranged over the proximal portion of the soleus muscle near its origin at the proximal fibula. The patient then tightens the strap 120.

In place of or in addition to the strap 120, the body 110 can partially or fully provide the necessary forces—particularly circumferential forces (hoop tension) to exert inwardly directed forces on the protrusion 130. The force applied to the leg by the protrusion 130 is preferably between about 1 and 10 pounds per square inch (about 7.0 kPa and 70.0 kPa). More preferably the force applied by the protrusion is between about 3 and 7 pounds per square inch (about 21 kPa and 50 kPa). In accordance with one preferred aspect, the force applied by the protrusion 130 is about 5 pounds per square inch (about 35.0 kPa).

The manner in which devices in accordance with the invention function is as follows. When the soleus muscle spasms, the spasming occurs near the proximal end thereof. The protrusion 130 impinges the soleus muscle at or below the spasming, effectively altering the end point of the muscle. The proximal portion thereof is allowed to relax to reduce spasming. The strap portion 120 also moves the fibula forward, reducing tension on the peroneal nerve.

As best seen in FIGS. 3 and 5, the protrusion 130 is convexly shaped. In the illustrated embodiments, the protrusion 130 is constructed from a substantially rigid back portion 331, and one or more layers 336, 339 of resilient material. In the illustrated embodiment, the protrusion assembly 130 is placed between the body 110 and the strap 120 (e.g., 120b in FIG. 3), and held in place by stitching 129, which advantageously can be sufficiently strong so as to secure the strap portion 120b to the body 110. The back portion 331 provides a stable backing for distributing forces against the strap 120. The convex contour of the inner portion of the protrusion 130 is configured so as to reduce excessive concentration of forces that might cause injury to the patient. The protrusion 130 can be made of a resilient material, such as a foam rubber. Alternatively, the protrusion can include a resilient gel-filled chamber. In accordance with one aspect of the invention, the protrusion 130 covers an area of between about 1.5 and 4.0 square inches (about 9.7-26.0 square centimeters).

The protrusion or "build-up" 130 is positioned on the body 110, in the posterior lateral portion of the orthopaedic appliance so that in position, the protrusion 130 impinges the calf musculature at the proximal portion of the soleus muscle at its origin near the proximal fibula.

The mechanism by which the subject orthopaedic appliance works is as follows. When the soleus muscle spasms, the spasming typically occurs near the proximal (superior) portion thereof. The build-up or protrusion on devices of the present invention place pressure distal to the muscle's origin on the tibia, and thus temporarily changes the end point of the muscle, allowing the more proximal (superior) portion to rest. This helps reduce or eliminate spasming. At the same time, tension exerted by the strap 120 urges the fibula forward into its normal position, which reduces tension on the peroneal nerve.

In its most simple form, the present invention can be embodied in any manner that exerts inwardly directed force on the proximal portion of the soleus muscle near its attachment point at the proximal fibula. Accordingly, the present invention can be embodied, for example, as a strap-shaped band with a protrusion, buildup or equivalent component on its inner surface.

In accordance with a further aspect, the invention includes a method of treating pain associated with neural tension on the peroneal (common fibular) nerve of a patient, including providing an orthopedic appliance having a protrusion on an inner surface thereof, orienting the orthopedic appliance so that the protrusion impinges a proximal portion of the soleus muscle of the patient near its origin at the proximal fibula, and applying pressure to the soleus muscle through the protrusion of the orthopedic appliance.

In the embodiment illustrated, the body 110 is between about 4.0 and 8.0 inches (about 10 and 20 centimeters) in height. In other preferred embodiments, the body 110 is between about 5.5 inches and 7.5 inches (about 14 and 19 centimeters) in height, and more preferably, depending on the precise embodiment, between about 6.3 and 6.7 inches (about 16 and 17 centimeters) in height.

Naturally, it is to be understood that variations in dimensions are possible, for example due to the variation in sizes of patient's legs. For example, a variety of ranges of sizes of the subject orthopaedic appliance 100 can be manufactured—for example, with circumferences being about as follows: small: 13.0-14.0 inches (33.0-35.5 cm); medium: 14.0-15.0 inches (35.5-38.0 cm); large: 15.0-16.0 inches (40.6 cm).

The methods and systems of the present invention, as described above and shown in the drawings, provide for an orthopaedic appliance with superior properties, which is capable of immediately relieving pain due to muscle spasming of the soleus muscle. The orthopaedic appliance fits just below the knee, and when tightened, applies pressure to the calf musculature—particularly the proximal soleus muscle near its attachment to the proximal fibula. The orthopaedic appliance also corrects displacement of the tibiofibular joint, by urging the fibula forward, correcting posterior displacement caused by spasming of the soleus muscle. This decreases the abnormal neural tension on the peroneal and sciatic nerve, which provides quick relief to low back and/or buttock pain.

It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. An orthopaedic appliance for reducing pathological tension on a patient's peroneal nerve, comprising:
    a cylindrical body configured for placement around a patient's leg below the popliteal crease;
    an adjustable strap assembly extending at least partially around the circumference of the cylindrical body; and
    a protrusion having a radially inwardly facing convex surface disposed between the cylindrical body and the adjustable strap assembly and located to apply pressure on a proximal portion of the patient's soleus muscle near its origin at the proximal fibula.

2. The orthopaedic appliance of claim 1, wherein the protrusion is positioned to apply pressure at a point between about 5.0 and 7.5 centimeters below the popliteal crease.

3. The orthopaedic appliance of claim 1, further comprising indicia on the body to guide placement of the orthopaedic appliance on the leg of the patient.

4. The orthopaedic appliance of claim 3, wherein the indicia is a marking on a front side of the body, placed to be in substantial alignment with a centerline of the patient's knee.

5. The orthopaedic appliance of claim 1, wherein the strap assembly includes a first strap portion extending laterally from a medial side of the body and a second strap portion extending from a dorsal side of the body, extending over the protrusion and toward the first strap portion.

6. The orthopaedic appliance of claim 5, further comprising a connecting element provided to secure the first strap portion to the second strap portion.

7. The orthopaedic appliance of claim 6, wherein the connecting element is a substantially rigid eyelet.

8. The orthopaedic appliance of claim 5, further comprising a repositionable fastener to allow adjustment of tension in the strap portions.

9. The orthopaedic appliance of claim 8, wherein the repositionable fastener is a hook-and-loop type fastener.

10. The orthopaedic appliance of claim 1, wherein the strap assembly includes a resilient band that extends at least partly around the circumference of the body.

11. The orthopaedic appliance of claim 1, wherein the strap assembly includes an adjustable band that extends at least partly around the circumference of the body.

12. The orthopaedic appliance of claim 11, wherein the adjustable band includes two portions.

13. The orthopaedic appliance of claim 1, wherein the strap assembly includes a resilient component in the body of the orthopaedic appliance for exerting hoop tension around the body, to maintain a sufficient amount of inwardly directed pressure on the protrusion to impinge the proximal portion of the soleus muscle at its tibial origin to release tension on and reduce spasming thereof.

14. The orthopaedic appliance of claim 1, wherein the protrusion includes a resilient portion on an inward-facing portion thereof.

15. The orthopaedic appliance of claim 1, wherein the protrusion is smoothly contoured.

16. The orthopaedic appliance of claim 1, wherein the protrusion includes a rigid portion on the outer side thereof for providing a stable backing to exert even pressure to the soleus muscle near its origin at the fibula.

17. The orthopaedic appliance of claim 1, wherein the body is formed of a compliant material which does not impede blood circulation.

18. The orthopaedic appliance of claim 17, wherein the body is formed of a neoprene rubber.

* * * * *